(12) United States Patent
Rosenberg et al.

(10) Patent No.: US 9,205,230 B2
(45) Date of Patent: Dec. 8, 2015

(54) ANCHORING A MEDICAL INSTRUMENT

(71) Applicant: INTERRAD Medical, Inc., Plymouth, MN (US)

(72) Inventors: Michael S. Rosenberg, Eagan, MN (US); Mark R. Christianson, Plymouth, MN (US); Kyle P. Taylor, Brooklyn Park, MN (US); Andrew T. Forsberg, Plymouth, MN (US); Edward A. Barlow, Bloomington, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 460 days.

(21) Appl. No.: 13/792,673

(22) Filed: Mar. 11, 2013

(65) Prior Publication Data

US 2013/0190727 A1 Jul. 25, 2013

Related U.S. Application Data

(60) Division of application No. 13/410,786, filed on Mar. 2, 2012, now Pat. No. 8,394,066, which is a continuation of application No. 13/229,394, filed on Sep. 9, 2011, now Pat. No. 8,137,323, which is a continuation of application No. 12/273,864, filed on Nov. 19, 2008, now Pat. No. 8,029,476.

(51) Int. Cl.
*A61M 5/32* (2006.01)
*A61M 25/04* (2006.01)
(Continued)

(52) U.S. Cl.
CPC ............ *A61M 25/04* (2013.01); *A61M 25/0097* (2013.01); *A61M 25/02* (2013.01); *A61M 2025/028* (2013.01); *A61M 2025/0286* (2013.01); *A61M 2025/0293* (2013.01)

(58) Field of Classification Search
CPC . A61M 25/04; A61M 25/0097; A61M 25/02; A61M 2025/028; A61M 2025/0286; A61M 2025/0293
USPC ....................................................... 604/174
See application file for complete search history.

(56) References Cited

U.S. PATENT DOCUMENTS 6,428,513 B1 8/2002 Abrahamson
6,695,861 B1 2/2004 Rosenberg
(Continued)

FOREIGN PATENT DOCUMENTS

EP 0818178 1/1998
EP 1852140 11/2007
WO WO 2007/035482 3/2007

OTHER PUBLICATIONS

International Search Report and Written Opinion for International Application No. PCT/US2009/064975, dated Jul. 27, 2010, 11 pages.
(Continued)

*Primary Examiner* — Edelmira Bosques
(74) *Attorney, Agent, or Firm* — Fish & Richardson P.C.

(57) ABSTRACT

Some embodiments of a medical anchor device include an elongate body coupled with deployable subcutaneous anchors to secure a catheter instrument (or other medical instrument) in place relative to a skin penetration point. In some circumstances, the elongate body may be in the form of catheter hub body, and the subcutaneous anchors can be deployed from the hub body by adjustment of a movable actuator. A locking member can interact with the actuator so as to retain the actuator in the deployed orientation during the medical procedure.

20 Claims, 15 Drawing Sheets

(51) Int. Cl.
*A61M 25/00* (2006.01)
*A61M 25/02* (2006.01)

(56) References Cited

U.S. PATENT DOCUMENTS

| 6,918,919 | B2 | 7/2005 | Krag |
| 2001/0041915 | A1 | 11/2001 | Roue et al. |
| 2002/0068899 | A1 | 6/2002 | McGuckin et al. |
| 2004/0074491 | A1 | 4/2004 | Hendricksen et al. |
| 2005/0187578 | A1 | 8/2005 | Rosenberg et al. |
| 2005/0234512 | A1 | 10/2005 | Nakao |
| 2007/0078397 | A1 | 4/2007 | Weststrate |
| 2007/0239138 | A1 | 10/2007 | Lawrence et al. |
| 2007/0249999 | A1 | 10/2007 | Sklar et al. |

OTHER PUBLICATIONS

International Preliminary Report on Patentability for International Application No. PCT/US2009/064975, Jun. 3, 2011, 6 pages.

Extended European Search Report for European Application No. 09828161, mailed Nov. 23, 2012.

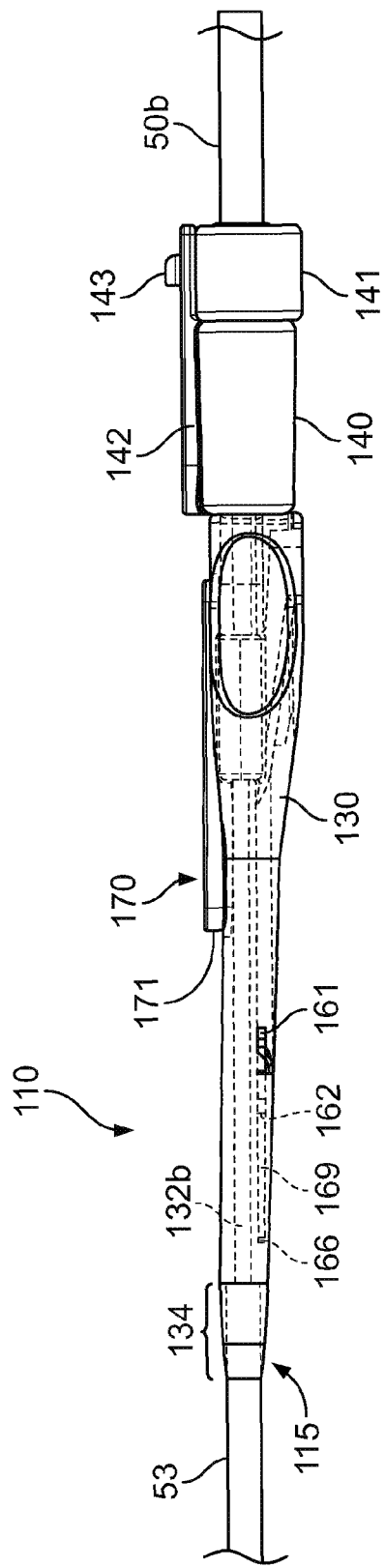

ANCHORING A MEDICAL INSTRUMENT

CROSS-REFERENCE TO RELATED APPLICATION(S)

This is a division of U.S. patent application Ser. No. 13/410,786 filed on Mar. 2, 2012 and entitled "Anchoring a Medical Instrument," which is a continuation of U.S. patent application Ser. No. 13/229,394 filed on Sep. 9, 2011 and entitled "Anchoring a Medical Instrument," which is a continuation of U.S. patent application Ser. No. 12/273,864 filed on Nov. 19, 2008 and entitled "Anchoring a Medical Instrument," the contents of which are fully incorporated herein by reference.

TECHNICAL FIELD

This document relates to an anchor device, such as a device for use in securing the position of a catheter instrument.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Following introduction into the patient, the catheter is secured to the patient. In some common practices, the catheter is secured to the patient using an adhesive tape on the skin or by suturing a catheter hub to the patient's skin.

SUMMARY

Some embodiments of a medical anchor device include a main body coupled with deployable subcutaneous anchors to secure a catheter instrument, or other medical instrument, in place relative to a skin penetration point. In some circumstances, the main body may be in the form of catheter hub body, and the subcutaneous anchors can be deployed from the hub body by adjustment of a movable actuator. The actuator can be adjusted relative to the hub body so that subcutaneous anchors deploy under the skin in a subcutaneous layer proximate to a skin penetration point, e.g., the entry point of the catheter instrument or another skin opening. A locking member can interact with the actuator so as to retain the actuator in the deployed orientation during the medical procedure. Such a configuration can allow the anchors to remain deployed in the subcutaneous region to secure the position of the catheter instrument while also reducing the likelihood of inadvertent withdrawal of the anchors before completion of the procedure.

In particular embodiments, a system for subcutaneously anchoring a catheter instrument may include a catheter hub body that provides fluid communication from one or more catheter lines to a distal catheter portion that is insertable through a skin penetration point. The system may also include a subcutaneous anchor mechanism movably coupled to the catheter hub body. The subcutaneous anchor mechanism may have one or more flexible anchors that extend outwardly away from the catheter hub body when in a deployed orientation in a subcutaneous layer proximate to the skin penetration point. The system may further include an actuator that is manually adjustable relative to the catheter hub body so as to shift the flexible anchors from a non-deployed orientation to the deployed orientation. The system may also include a locking device that is movable relative to the actuator so as to shift from an actuator-unlocked position to an actuator-locked positioned in which the locking device is arranged between the catheter hub body and the actuator when the flexible anchors are in the deployed orientation.

In some embodiments, a medical anchoring system may include an elongate body that provides fluid communication from an internal lumen to a distal catheter portion that is insertable through a skin penetration point. The system may also include a subcutaneous anchor mechanism movably coupled to the elongate body. The subcutaneous anchor mechanism may include flexible anchors that are adjustable between a non-deployed orientation in which the flexible anchors at least partially reside inside the elongate body and a deployed orientation in which the flexible anchors extend outwardly from the elongate body into a subcutaneous layer proximate to the skin penetration point. The system may further include an actuator including an external portion that is movable away from the elongate body so as to shift the flexible anchors from the non-deployed orientation to the deployed orientation. Also, the system may include a locking device that is manually movable to fit in a gap between the elongate body and the external portion of the actuator when the flexible anchors are in the deployed orientation.

Some embodiments can include a method of anchoring a catheter instrument. The method may include inserting at least a portion of a catheter hub body through a skin penetration point so that a distal catheter portion extending from the catheter hub body is advanced into a blood vessel. The method may also include adjusting an actuator to an operative position relative to the catheter hub body so as to deploy a subcutaneous anchor mechanism in a subcutaneous layer proximate to the skin penetration point. The subcutaneous anchor mechanism may comprise one or more flexible anchors that extend outwardly from the catheter hub body to abut an underside of a skin layer when deployed in the subcutaneous layer. The method may further include moving a locking device relative to the actuator and the catheter hub body so that the locking device retains the actuator in the operative position.

These and other embodiments may provide one or more of the following advantages. First, some embodiments of an anchor system can retain a catheter instrument in an operative position relative to a skin penetration point without necessarily requiring sutures or skin adhesives. Second, some embodiments of an anchor system can reduce the likelihood of damage to a skin layer, such as a subcutaneous skin layer, when the anchor system is deployed to retain a catheter instrument in an operative position relative to a skin penetration point. Third, some embodiments of an anchor system include a locking mechanism that minimizes the likelihood of one or more of the anchors shifting to a non-deployed position without user intervention.

The details of one or more embodiments are set forth in the accompanying drawings and the description below. Other features, objects, and advantages will be apparent from the description and drawings, and from the claims.

DESCRIPTION OF DRAWINGS

FIG. 8A is a side view of the medical anchor system of FIG. 1.

Like reference symbols in the various drawings indicate like elements.

DETAILED DESCRIPTION OF ILLUSTRATIVE EMBODIMENTS

An anchor system can hold one or more lumens in proximity to a skin penetration site. The anchor system can include subcutaneous anchors that can be activated from a non-deployed configuration to a deployed position to engage bodily tissue in a subcutaneous region under the skin and hold the anchor system in place. In some embodiments, the anchor system can include a main body coupled to one or more catheter lumens to thereby cooperatively hold the main body and catheter lumens in place relative to the skin penetration site. The anchors can be retracted from a deployed configuration to a non-deployed configuration so that damage to surrounding subcutaneous tissue is minimized when the anchor system is withdrawn from the patient's skin.

Figure 1:
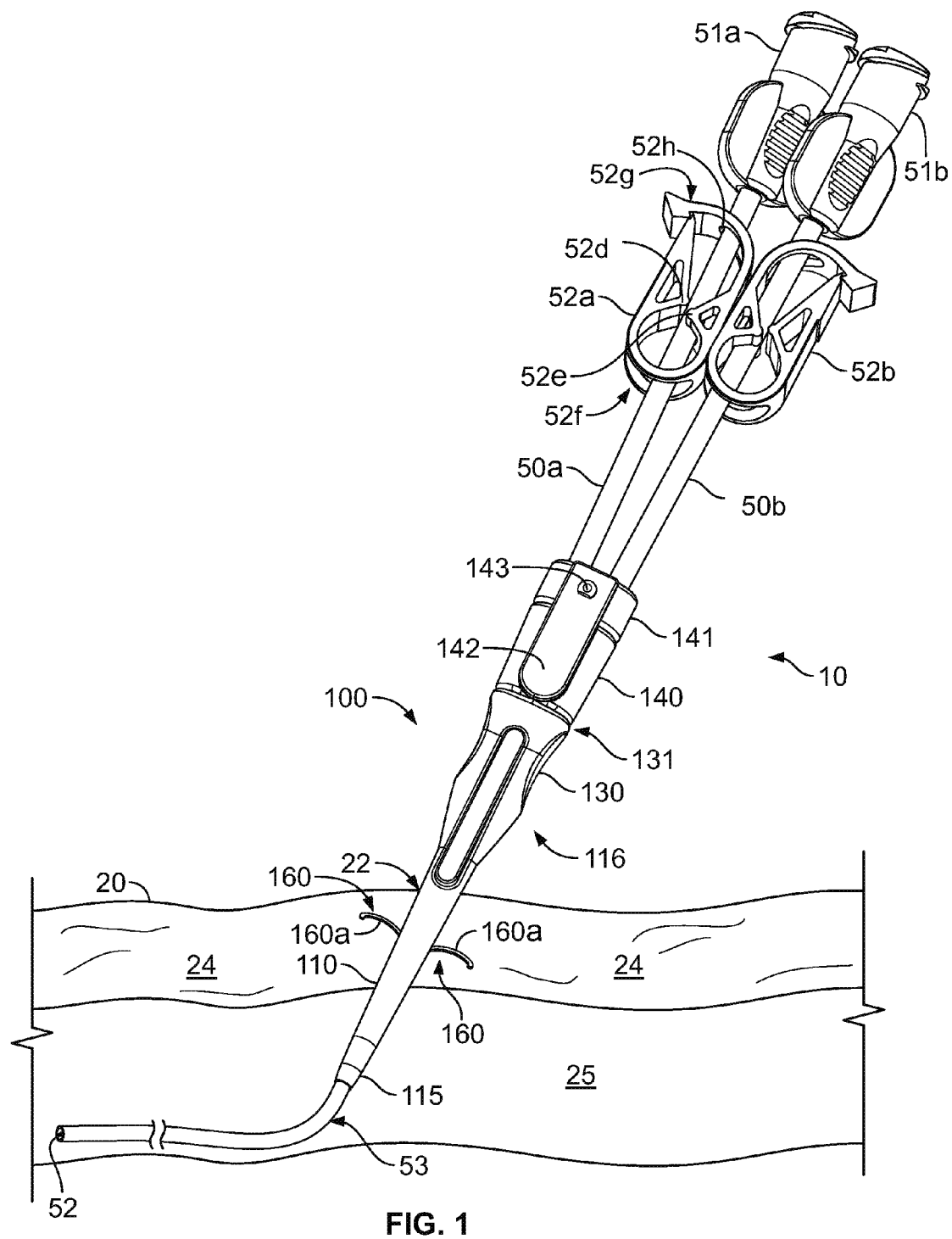
FIG. 1 is a perspective view of a medical anchor system having a subcutaneous anchor mechanism, in accordance with some embodiments.

Referring to FIG. 1, some embodiments of a medical anchor system 10 include an anchor device 100 and one or more catheter lines 50a, 50b (collectively referred to as catheter 50) (or other medical instrument) that extend though one or more working channels of the anchor device 100. The anchor device 100 may include a hub body, which can be in the form of an elongate body 110, that receives at least a portion of the catheter 50 and houses one or more subcutaneous anchors 160. As described below, the anchors 160 may be deployable such that they extend from the elongate body 110. The anchor device 100 includes a distal tip portion 115 that may penetrate through a skin penetration site 22 and into a subcutaneous layer 24 adjacent to a skin portion 20. Also, the anchor device 100 includes a proximal portion 116 that can remain external to the skin portion 20. In this embodiment, portions of the catheter 50 extend from the proximal portion 116 so as to allow other, external lumen-type devices (not shown in FIG. 1) to be attached to the one or more catheter lines 50a, 50b. The catheter 50 includes a distal catheter portion 53 extending from the distal tip portion 115 of the elongate body 110. The distal catheter portion 53 is configured to be advanced into a blood vessel 25 or other bodily lumen of a human or animal patient and toward a targeted body site inside the patient's body. As described in more detail below, the distal catheter portion 53 provides fluid communication from the one or more catheter lines 50a, 50b to the blood vessel 25. For example, the distal catheter portion 53 may include a plurality of internal lumens (e.g., coaxial or adjacent) extending toward the catheter tip 52. Thus, the catheter line 50a may be in fluid communication with a first internal lumen of the distal catheter portion 53, and the second catheter line 50b may be in fluid communication with a second internal lumen of the distal catheter portion 53. Alternatively, the first and second catheter lines 50a and 50b can be in fluid communication with the same internal lumen of the distal catheter portion 53. In other embodiments in which the hub body 110 receives a single catheter line (e.g., single lumen PICC device or the like), the hub body 110 can include a lumen that provides fluid communication between the single catheter line and the internal lumen of the distal catheter portion 53.

The anchor device 100 can be used to retain the catheter 50 near the skin penetration site 22. In particular, the elongate body 110 can house the one or more anchors 160. As described in more detail below, the anchors 160 may comprise one or more flexible tines 160a that are deployable into the subcutaneous layer 24 under the skin portion 20 so as to retain the position of the anchor device 100 relative to the skin penetration site 22.

In this embodiment, the anchor device 100 includes an actuator 141 that adjusts the anchors 160 from a non-deployed position (FIG. 2) to the deployed position depicted in FIG. 1. The actuator 141 may operate as a sliding mechanism that reciprocates along a portion of the catheter lines 50a and 50b near the elongate body 110. As discussed in greater detail below, a portion of the actuator 141 includes an actuator rod 164 (FIG. 10) that deploys and retracts the anchors 160 by reciprocating along an interior actuator channel 169 (FIG. 7) of the elongate body 110 between a distal position and a proximal position. A user may insert the elongate body 110 through the skin penetration site 22 so that one or more anchor deployment ports 165 (FIG. 9) are arranged under the skin portion 20 in the subcutaneous layer 24. For example, the anchor device 100 may penetrate the skin portion 20 through a small incision made by a physician. In some cases a dilation instrument (not shown in FIG. 1) may be used to assist in advancing the anchor device 100 through the incision. During insertion, the anchors 160 are in the non-deployed position, being substantially encased within the anchor device 100. The anchors can be placed in the non-deployed position by shifting the actuator 141 to a distal position, where the actuator 141 is moved away from the elongate body 110. After insertion, the distal catheter portion 53 and possibly the distal tip portion 115 of the elongate body 110 can be advanced into a targeted blood vessel 25 or other body lumen. When the anchor device 100 is arranged in the desired position, the user can apply a force to the actuator 141 so as to slide the actuator 141 from the distal position to a proximal position (refer to FIGS. 2-3). As described in more detail below, the adjustment of the actuator 141 causes the flexible tines 160a to shift from a non-deployed position to the deployed position shown in FIG. 1. Also described in more detail below, the actuator 141 can be secured in the proximal position using a lock 140 that is movably connected to the actuator 141 (e.g., pivots about a pivot member 143 in this embodiment). The lock 140 can minimize the likelihood of the anchors 160 inadvertently retracting to a non-deployed position until the anchor device 100 is ready to be withdrawn from the subcutaneous layer 24.

Still referring to FIG. 1, in some embodiments, one or more flow restriction devices 52a, 52b can control fluid flow through the catheter 50. In this embodiment, each flow restriction device 52a, 52b includes a resiliently flexible member 52f configured to compress upon an associated catheter line 50a or 50b. The flow restriction devices 52a, 52b can include one or more ports 52h through which catheter line 50a can pass such that the flow restriction device 52a, 52b are slidable along a length of the catheter 50 when in an unlocked configuration. In this embodiment, the resiliently flexible member 52*f* includes one or more opposing protrusions 52*d*, 52*e* which exert a squeezing force on the catheter 50 when the resiliently flexible member 52*f* is compressed upon the catheter 50. Fluid flow through the catheter can be adjusted by applying a requisite pressure to the catheter via the opposing protrusions 52*d*, 52*e*. A locking mechanism 52*g* can hold the relative position of the opposing protrusions 52*d*, 52*e* in a chosen position so that a chosen level of fluid flow can be maintained over a period of time without further user intervention.

In some cases, the proximal ends of catheter lines 50*a*, 50*b* each terminate into a catheter coupling member 51*a*, 51*b* (collectively referred to as coupling member 51) respectively. The catheter coupling member 51 can be used to connect one or more of the catheter lines 50*a*, 50*b* to another catheter (not shown) or another type of medical device having a lumen, including a pump system. Catheter coupling members 51*a*, 51*b* can permit a range of fluid delivery and sampling systems to be connected to the medical device anchor system 10 without necessarily requiring a new anchoring system to be inserted into the patient each time. Such a configuration can be useful for patients who receive a PICC line for infusion of various medications or withdrawing bodily fluids (without repeated insertion of syringe needles into the patient).

Still referring to FIG. 1, the anchor device 100 includes the anchors 160 for use in the temporary anchoring of at least a portion of elongate body 110 in the subcutaneous layer 24 under the skin portion 20. In some embodiments, the anchors 160 may comprise a material that exhibits superelasticity. As such, the anchors 160 can flexibly shift from a non-deployed position (FIG. 2) to a deployed position (FIG. 1) when in the subcutaneous layer 24 of the skin portion 20. For example, the anchors 160 may be formed from a length of nitinol wire or from a sheet of nitinol material, which has been processed to exhibit superelasticity below or at about a normal human body temperature, such as below or at about 37 degrees Celsius. The nitinol material may comprise, for example, Nickel Titanium (NiTi), Niobium Titanium (NbTi), or the like. Alternatively, the anchors 160 may comprise a metal material such as stainless steel, spring steel, titanium, MP35N and other cobalt alloys, or the like. In these embodiments, the anchors 160 can be formed from a material or materials that allow them to be adjustable from the non-deployed position to the deployed position as shown in FIG. 1.

In some embodiments, the anchors 160 can be flexed to a stressed condition when in the non-deployed position, e.g., prior to placement of the anchor device 100 in a patient. For example, as described below in connection with FIG. 2, the anchors 160 may be retracted into an internal space of the elongate body 110 when in the non-deployed position. When deployed, as shown in FIG. 1, the anchors 160 can return toward a shape (e.g., by exhibiting superelastic characteristics) that allow the anchors 160 to secure the elongate body 110 relative to the skin penetration site 22 for a period of time until the treatment with the catheters 50 is completed.

The anchors 160 may be designed with a curvature that facilitates the transition from the non-deployed to the deployed position. Furthermore, the curvature of the anchors 160 may be configured to eliminate or reduce the potential damage to the skin during deployment of the anchors 160. For example, the anchors 160 may include a convex curvature that abuts against the underside of the skin portion 20 in a manner that prevents the flexible tines 160 from piercing through the underside of the skin portion 20. When the anchors 160 extend from the anchor deployment ports 165 (refer to FIGS. 7-9) positioned in the subcutaneous layer 24, the curved shape of the anchors 160 can allow them to deploy adjacent to the skin portion 20 while reducing the likelihood of tearing or otherwise damaging the skin portion 20. When deployed, the anchors 160 can serve to retain the elongate body 110 of the anchor device 100 relative to the skin penetration site 22. In some embodiments, the anchors 160 may provide a holding force of about 1 lb. or greater, depending upon the medical procedure being performed, the materials comprising the anchors 160, the geometry of the anchors 160, and/or other factors. For example, the anchors 160 may provide a holding force of about 0.5 lbs or more, about 1 lb to about 20 lbs, about 1 lb to about 5 lbs, or about 2 lbs to about 3 lbs.

In use, the anchors 160 can be shifted to the non-deployed position (refer, for example, to FIG. 2) prior to insertion so as to minimize resistance and possible damage to the skin portion 20 when a portion of elongate body 110 is inserted through the skin penetration site 22. In some cases, the medical device anchor system 10 can be shipped to the intended user (e.g., a physician or other healthcare provider), with the anchors 160 in the non-deployed position, so that the anchor device 100 can be readily inserted into the skin portion 20 without necessarily requiring the user to shift the actuator 141. When the anchor device 100 has been inserted to the intended depth inside the subcutaneous layer 24, the anchors 160 can be shifted to the deployed position (refer, for example, to FIG. 1) to provide at least temporary anchoring for the anchor device 100. When removal of the anchor device 100 is desired, the anchors 160 can be shifted back to the non-deployed position (e.g., by adjustment of the actuator 141) to reduce the likelihood of withdrawal resistance and possible damage to the skin portion 20 during removal.

Figure 2:
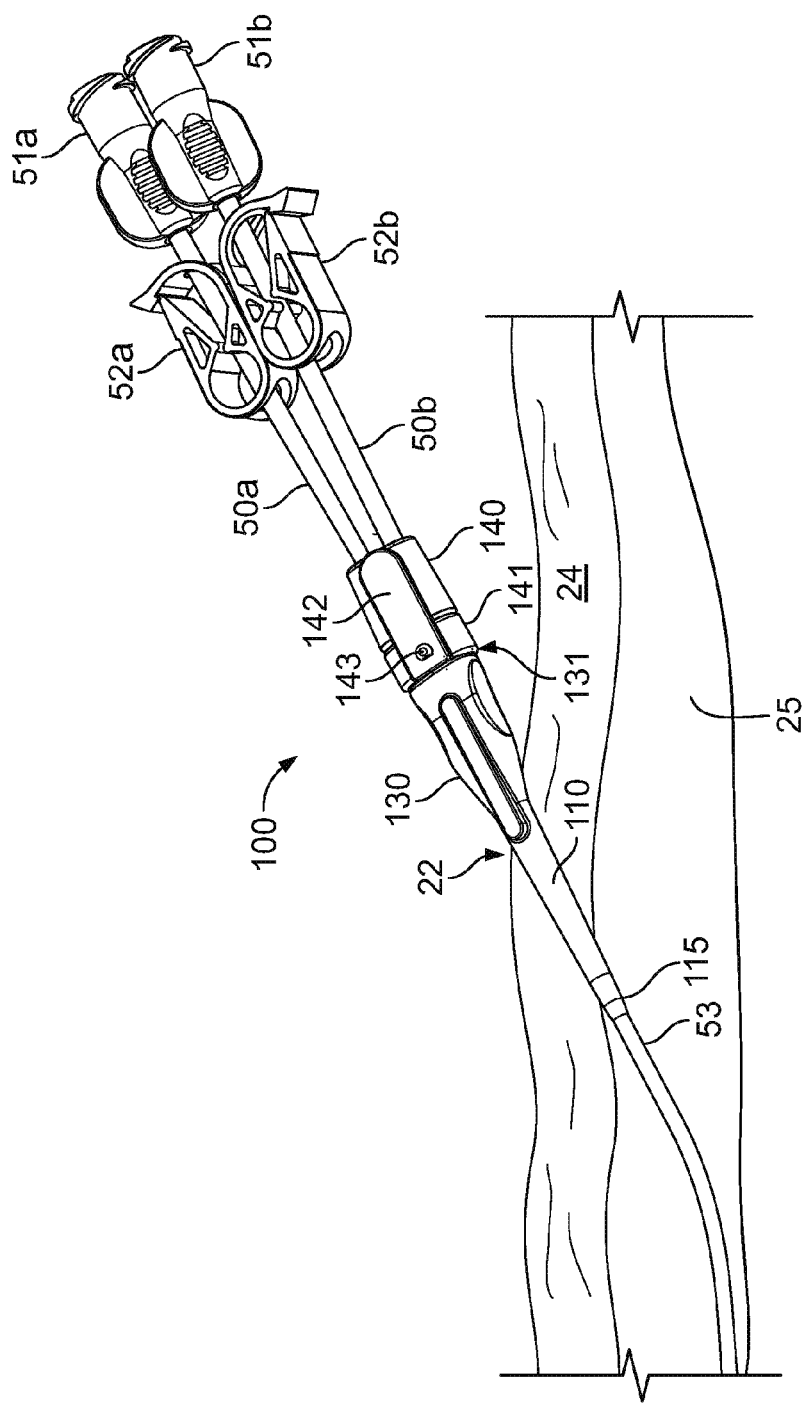
FIGS. 2-6 illustrate exemplary operations for deploying and locking the subcutaneous anchor mechanism of the medical anchor system of FIG. 1.
Figure 3:
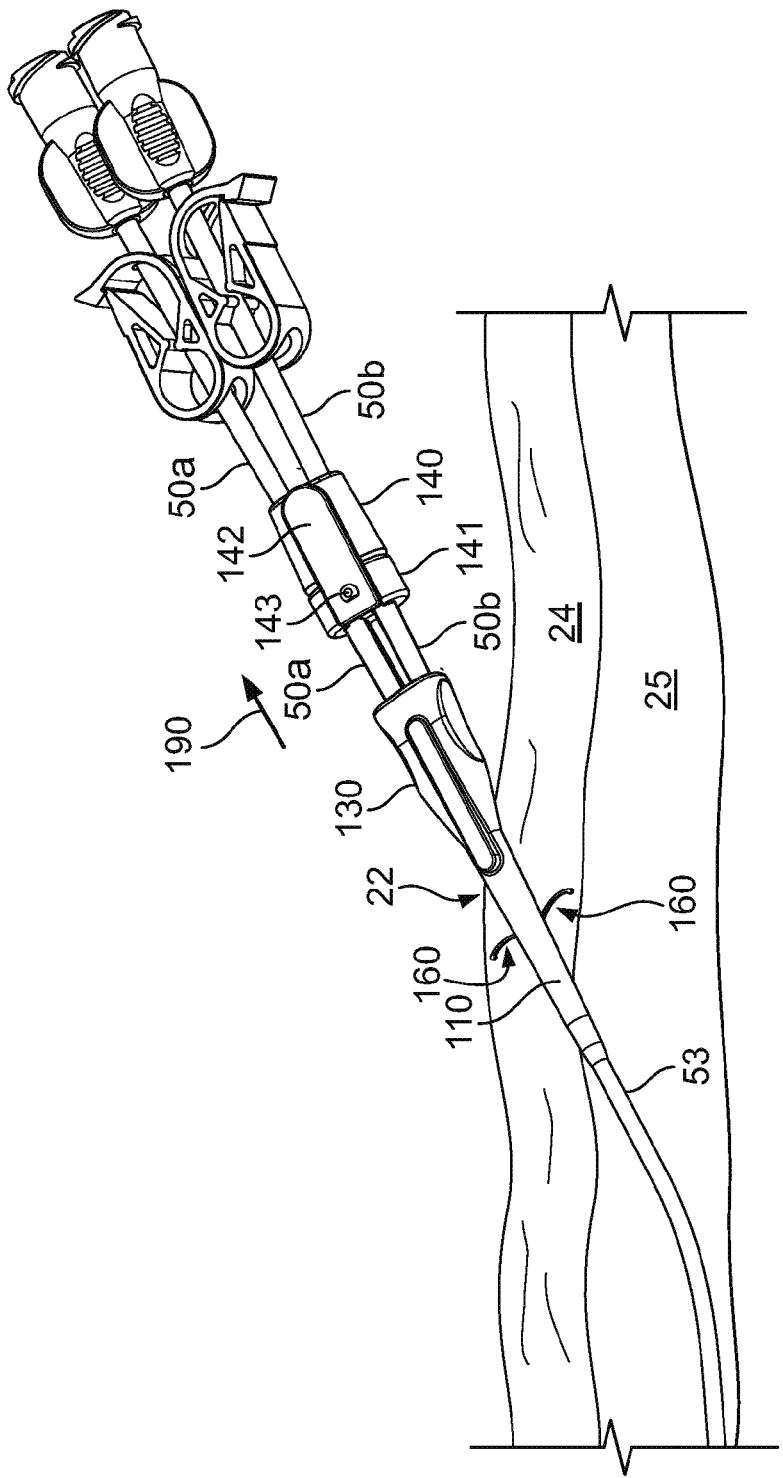

Referring now to FIGS. 2-6, some embodiments of the medical device anchor system 10 can be configured with the lock 140 movably coupled to the actuator 141 (e.g., rotatably coupled about the pivot member 143 in this embodiment). The lock 140 can be used to secure the actuator 141 in a selected configuration such that the anchors 160 remain in the deployed position. Referring to FIG. 2, the anchor device 100 is in a non-deployed and non-locked configuration. In particular, the anchors 160 are retained inside an internal space of the elongate body 110 in a non-deployed position. The elongate body 110 can include the anchor deployment ports 165 (FIG. 7) through which the anchors can be extended and retracted in response to movement of the actuator 141. In this configuration, the actuator 141 is arranged in a distal position (FIG. 2) before it is slidably adjusted in a longitudinal direction 190 to a proximal position (FIG. 3). Also in this configuration, the lock 140 is arranged in a first rotational position in which it is positioned proximal to the actuator 141.

When the anchor device 100 is in the non-deployed and non-locked configuration (FIG. 2), the distal tip portion 115 of the elongate body 110 can be readily inserted through the skin penetration site 22 (refer to FIG. 1) without interference from the anchors 160. In a preferred embodiment, the catheter 50 is fixedly coupled to the elongate body 110 as described in greater detail below. As such, the catheters lines 50*a*, 50*b* can remain affixed to the elongate body 110 during the time that the elongate body 110 remains anchored to the skin portion 20, and various other fluid supplying or sampling lumens can be connected via the catheter coupling members 51*a*, 51*b*. In alternative embodiments, the anchor device 100 may act as a sleeve so that the elongate body 110 has a channel to releasably receive a separate catheter or instrument after the sleeve is seated at the skin penetration site 22.

Referring now to FIG. 3, the anchor device 100 can be adjusted to a deployed and non-locked configuration. In this configuration, the anchors 160 are deployed from their respective anchor deployment ports 165 (FIG. 7) so as to extend outwardly from the elongate body 110 of the anchor device 100. In particular, the anchors 160 are shifted to the deployed position when the actuator 141 is moved in the longitudinal direction 190 to the proximal position. The actuator 141 can be pulled by a user to slide the actuator 141 toward the proximal position. The movement of the actuator 141 transmits a deployment force to the anchors 160 via the actuator rod 164 (FIG. 10), so that the anchors 160 at least partially extend out of the anchor deployment ports 165. As previously described, the flexible tines 160a can include a curved shape that facilitates the transition from the non-deployed to the deployed position and reduces the likelihood of damaging the underside of the skin portion 20 during deployment in the subcutaneous layer 24 (FIG. 1). Anchor tines 160a may be disposed proximal to the anchor deployment ports 165 such that when the actuator rod 164 is drawn rearward (e.g., opposite the direction of the distal tip 115), a force is imparted to the anchor 160 which forces them to protrude from the anchor deployment ports 165.

Figure 4:
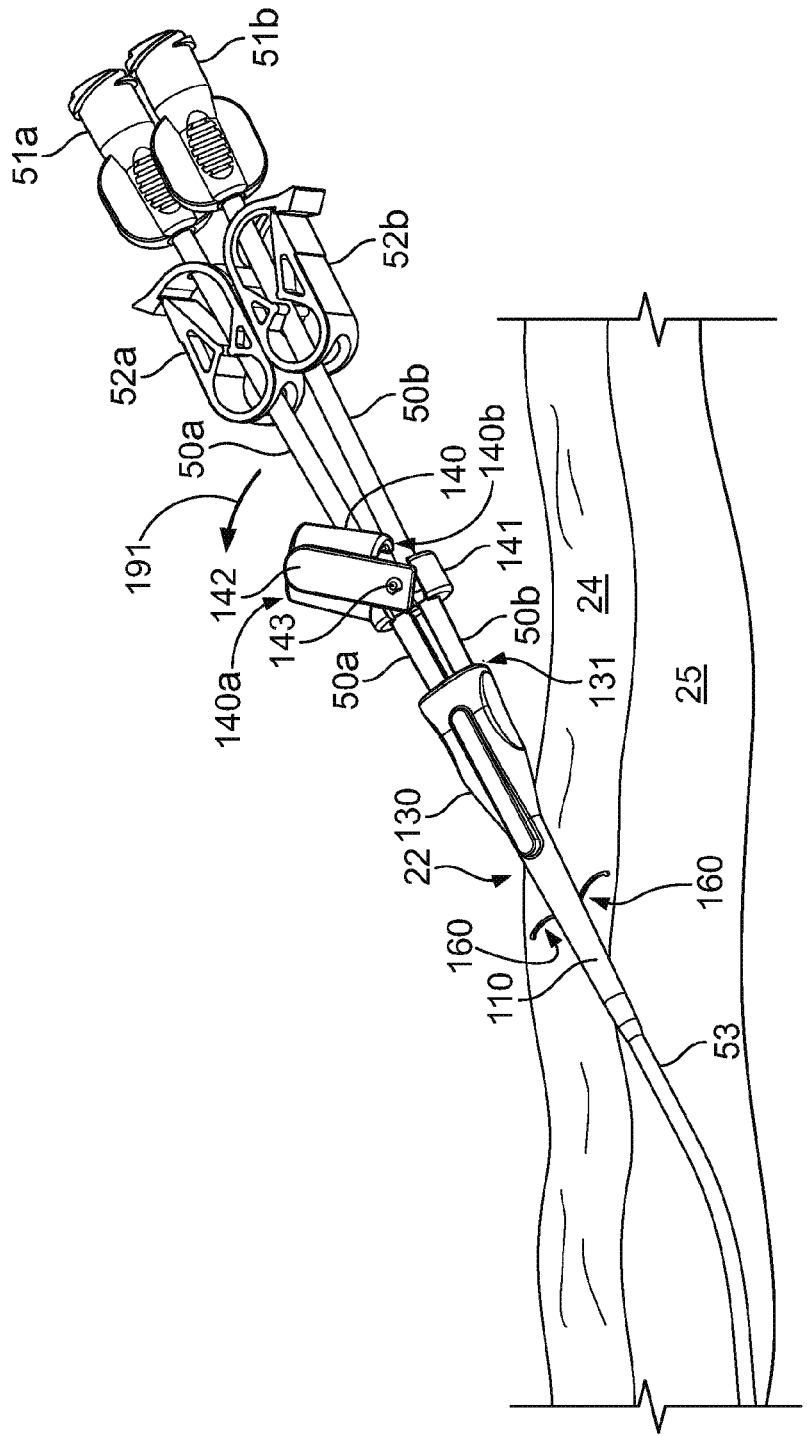
Figure 5:
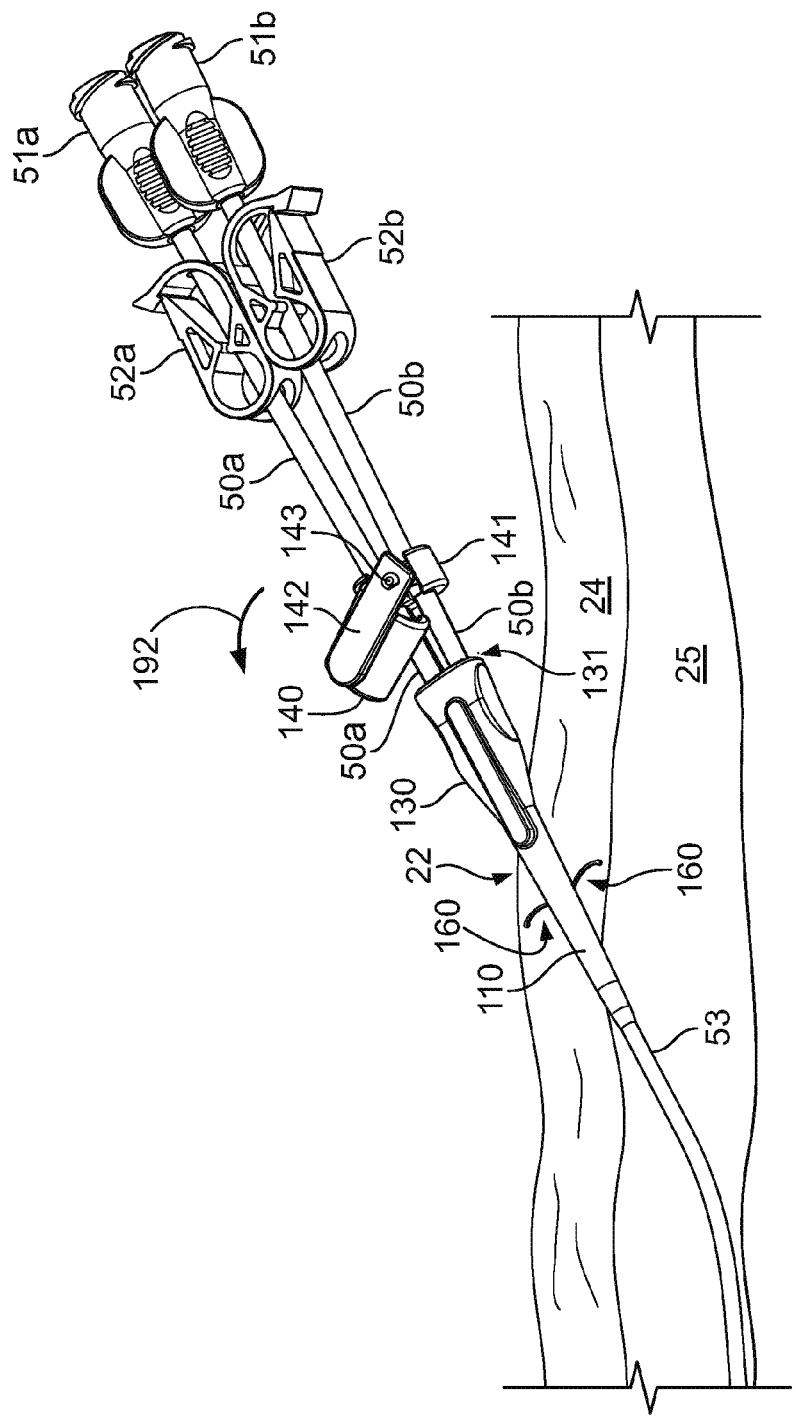
Figure 6:
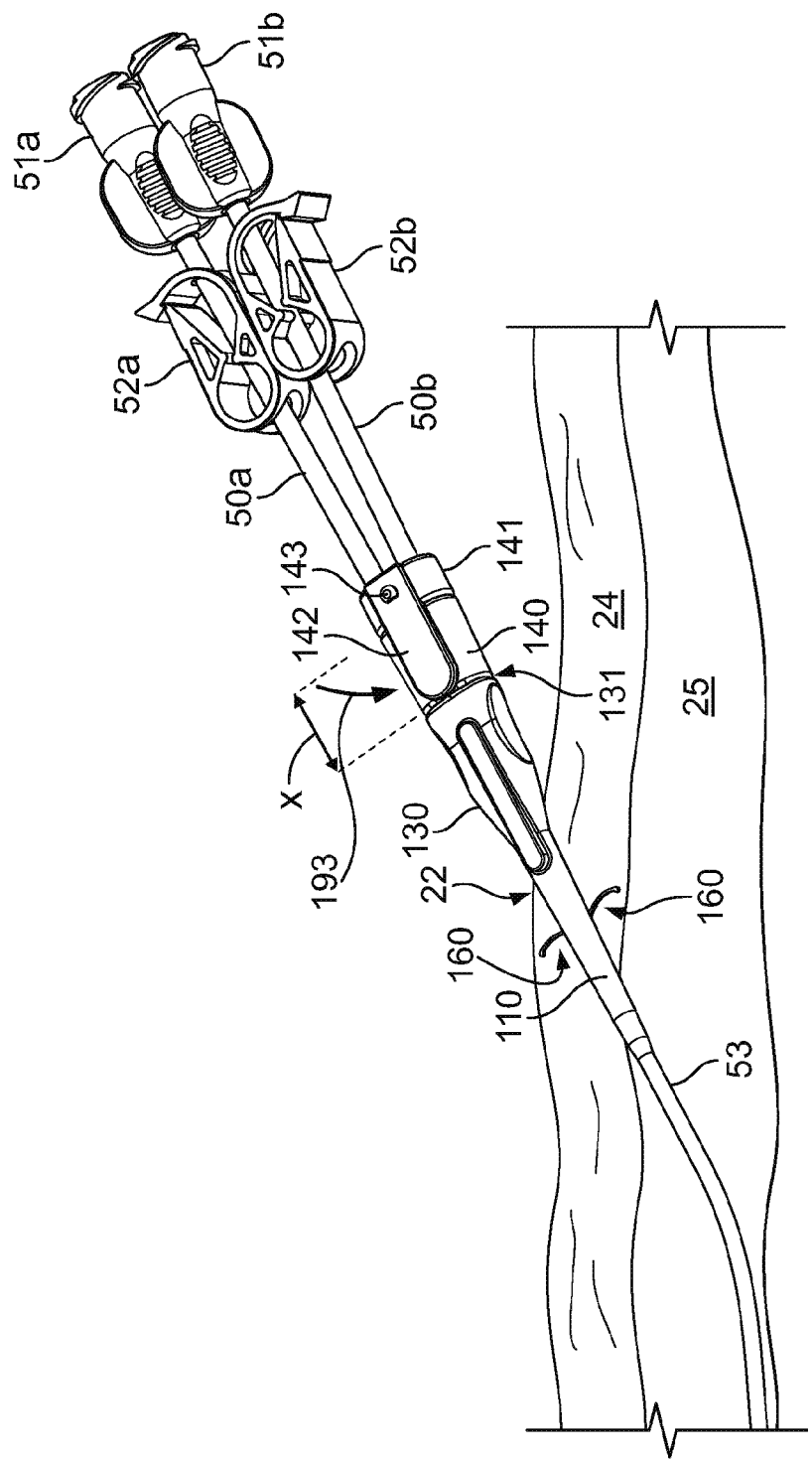

Referring now to FIGS. 4-6, the anchor device 100 can be adjusted from the deployed and non-locked configuration (FIG. 3) to a deployed and locked configuration (FIG. 6). The anchor device 100 can first be shifted to the deployed and non-locked configuration (as previously described in connection with FIG. 3). Lock 140 may be employed to hinder the actuator 141 from prematurely shifting back toward the distal position (FIG. 2), which might otherwise cause the anchors 160 to prematurely retract. In some embodiments, the lock 140 can provide a mechanical bracing force between the actuator 141 and a proximal surface 131 of the elongate body 110 that reduces the likelihood of the actuator 141 prematurely shifting to the distal position without user intervention. In this embodiment, lock 140 is coupled to a swing arm 142 that allows rotational pivoting of the lock 140 about the pivot member 143. The pivot member 143 can include an elongate shaft that extends through an aperture of the swing arm 142 to rotatably couple the swing arm 142 and the actuator 141. The pivot member 143 can include an end cap or retainer head so as to permit the swing arm 142 and the actuator 141 to be rotatably coupled while reducing the likelihood of separation.

Figure 11:
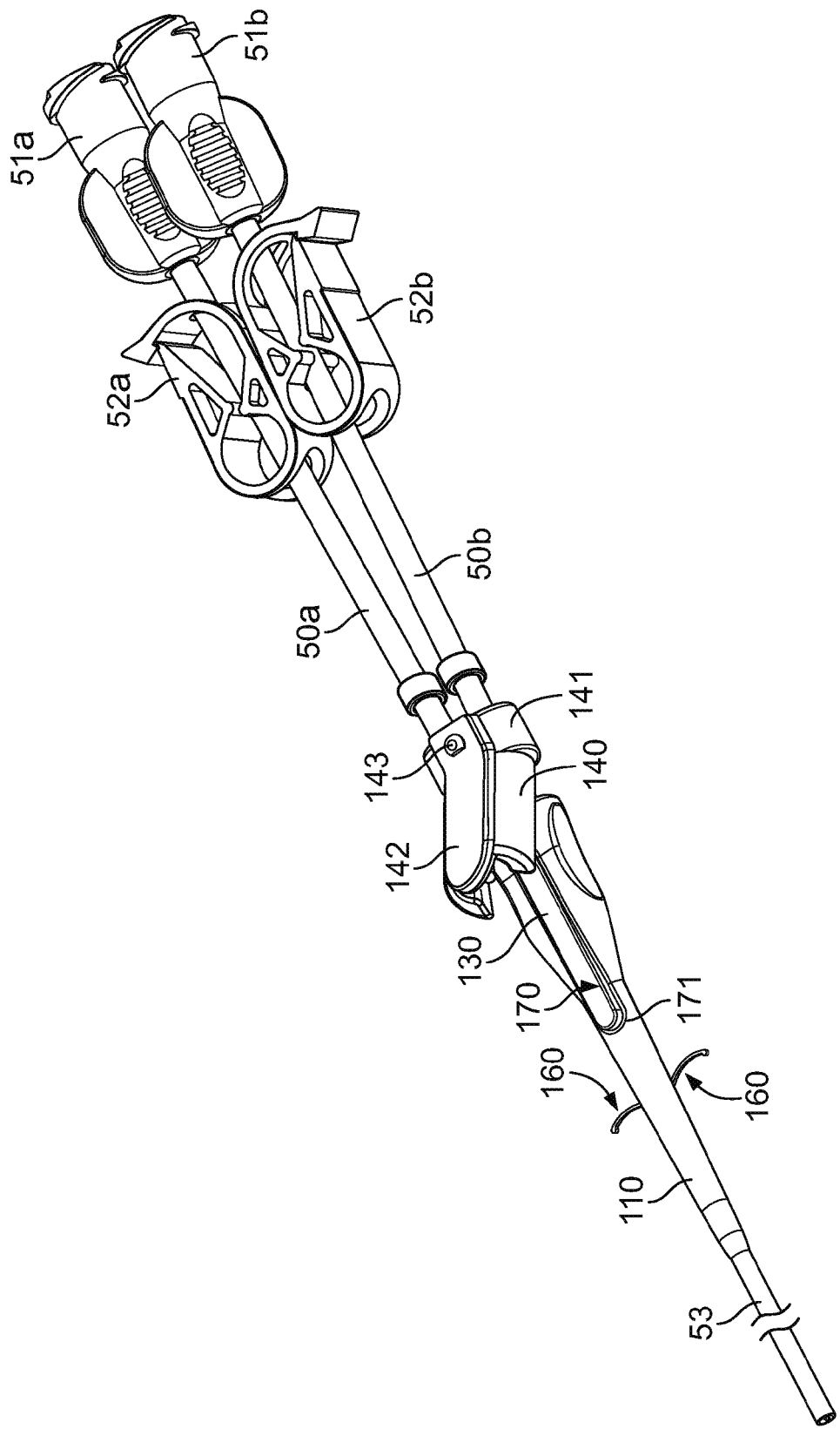
FIGS. 11-13 illustrate exemplary operations for deploying and locking the subcutaneous anchor mechanism of the medical anchor system, in accordance with alternative embodiments.

In this embodiment, the lock 140 and the swing arm 142 are made of a resiliently flexible material. For example, the lock 140 and the swing arm 142 can be integrally molded from a flexible polymer material. The lock 140 has curved portions 140a, 140b that substantially mate with an outer circumference of catheter lines 50a and 50b, respectively. The curved portions 140a, 140b circumferentially engage catheter lines 50a and 50b when in a locked configuration, thus reducing the likelihood of the lock 140 rotationally shifting from the proximal or distal position without user intervention. Because the lock 140 is made from a flexible material, curved portions 140a, 140b can flex outwardly when engaging or disengaging the lock 140 to or from the catheter lines 50a, 50b. Lock 140 can resiliently return to its original form after being flexed outwardly to either to remove or engage the lock 140 with the catheter lines 50a, 50b. Swing arm 142 is similarly resiliently flexible to allow the engagement and disengagement of the lock 140 with the catheter lines 50a, 50b. In this embodiment, swing arm 142 can flex from a substantially planar configuration when the lock 140 is engaged with catheter lines 50a, 50b (FIG. 1), to a curved configuration when the lock 140 is disengaged from the catheter lines 50a, 50b (FIG. 11).

As shown in FIG. 4, the anchor device 100 can be adjusted from the deployed and non-locked configuration (FIG. 3) to a deployed and locked configuration (FIG. 6) by first disengaging the lock 140 from catheter lines 50a, 50b while the lock 140 is in the proximal position. This may be accomplished by, e.g., exerting the requisite force (e.g., an upward force) on the lock 140 so that the curved portions 140a, 140b shift away from the catheter lines 50a, 50b. At this point the lock 140 and the swing arm 142 can rotate about the pivot member 143 so that the lock 140 is moved in a rotational direction 191.

As shown in FIG. 5, the lock 140 can be further moved by angular rotation 192 to place the lock 140 and the swing arm 142 in an intermediate distal position. As the lock 140 is being rotated from a fully proximal position (FIG. 3) to a fully distal position (FIG. 6), the position of the actuator 141 can remain substantially stationary relative to the elongate body 110, thus maintaining the deployed position of the anchors 160.

As shown in FIG. 6, when the lock 140 approaches the fully distal position (as denoted by angular rotation 193), the swing arm 142 and the lock 140 can be lifted slightly, allowing the curved portions 140a, 140b of the lock 140 to transition over the catheter lines 50a, 50b until the longitudinal axis of the swing arm 142 is substantially parallel with the longitudinal axis of the elongate body 110. A force can be applied to the swing arm 142 and the lock 140 so that the lock 140 snaps down and engages the catheter lines 50a, 50b in a locked configuration (FIG. 6). Once in the distal and locked position (FIG. 6), the lock 140 mates with the proximal surface 131 of the elongate body 110 so as to fit snugly between the elongate body 110 and the actuator 141. This configuration can reduce the likelihood of the actuator 141 prematurely shifting to a distal position (and premature withdrawal of the anchors 160).

In this embodiment, when the anchor device 100 is in a deployed and locked configuration (FIG. 6), various fluid delivery and sampling systems can be coupled with the medical device anchor system 10. For example, blood may be drawn from the catheter lines 50a, 50b; likewise, medications can be introduced into a patient's blood vessel 25 via the one or more catheter lines 50a, 50b. The medical device anchor system 10 may remain attached to the skin for an extended period of days, weeks, or months.

Figure 10:
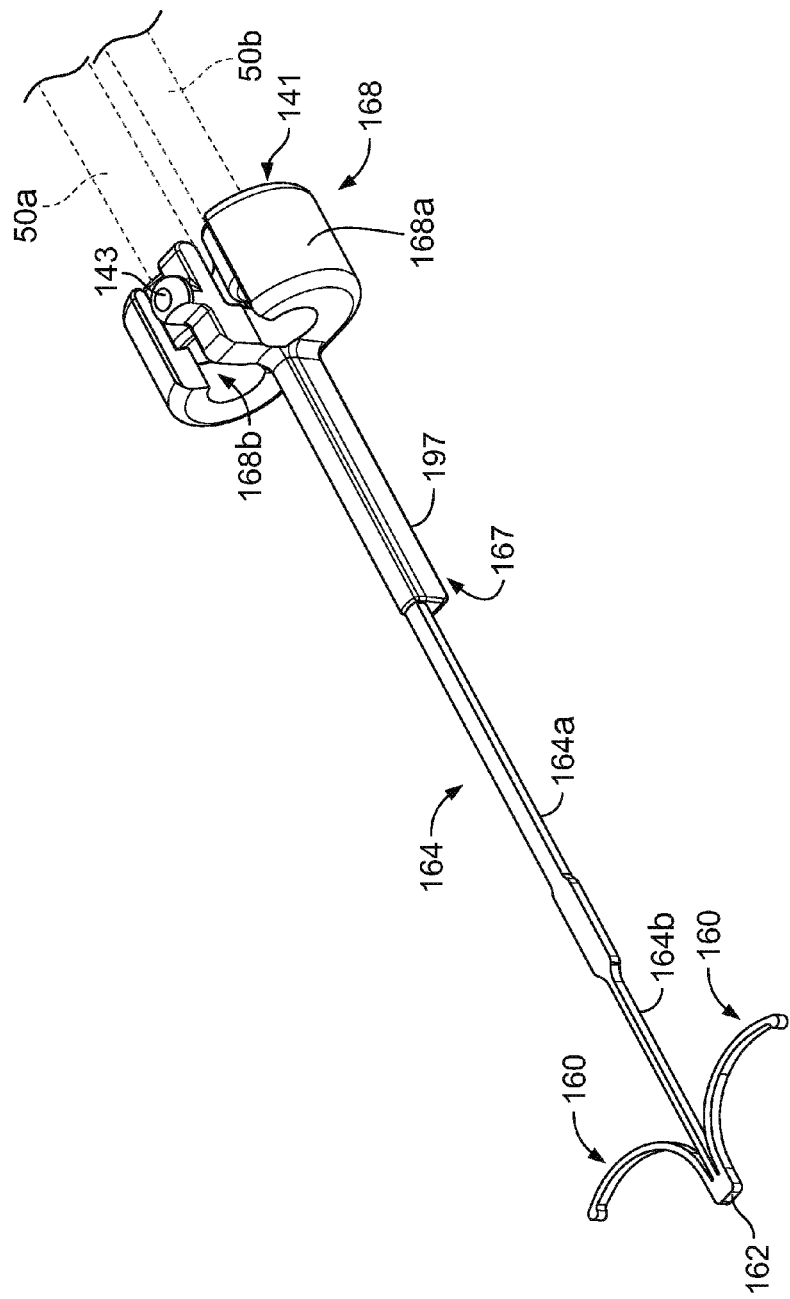
FIG. 10 is a perspective view of a portion of the medical anchor system of FIG. 1.

To remove the anchor device 100 from the patient, the process described for inserting the anchor device 100 (refer to FIGS. 2-6) described above can generally be reversed. For example, in this embodiment, to remove the anchor device 100 from the skin portion 20, the lock 140 can be lifted so as to disengage the catheter lines 50a, 50b. The lock 140 and swing arm 142 thus become free to rotate about the pivot member 143 as previously described. The lock 140 can be rotated from a distal position (FIG. 6) to a proximal position (FIG. 3). The user may choose to re-engage the lock 140 in the proximal position with the catheter lines 50a, 50b, however this step may be unnecessary if the user simply wishes to withdraw the anchor device 100 from the skin portion 20. With the lock 140 in a proximal position, the actuator 141 is free to shift from the proximal position to a distal position (FIG. 2), which has the effect of applying a translational force to the actuator rod 164 (FIG. 10).

Figure 7:
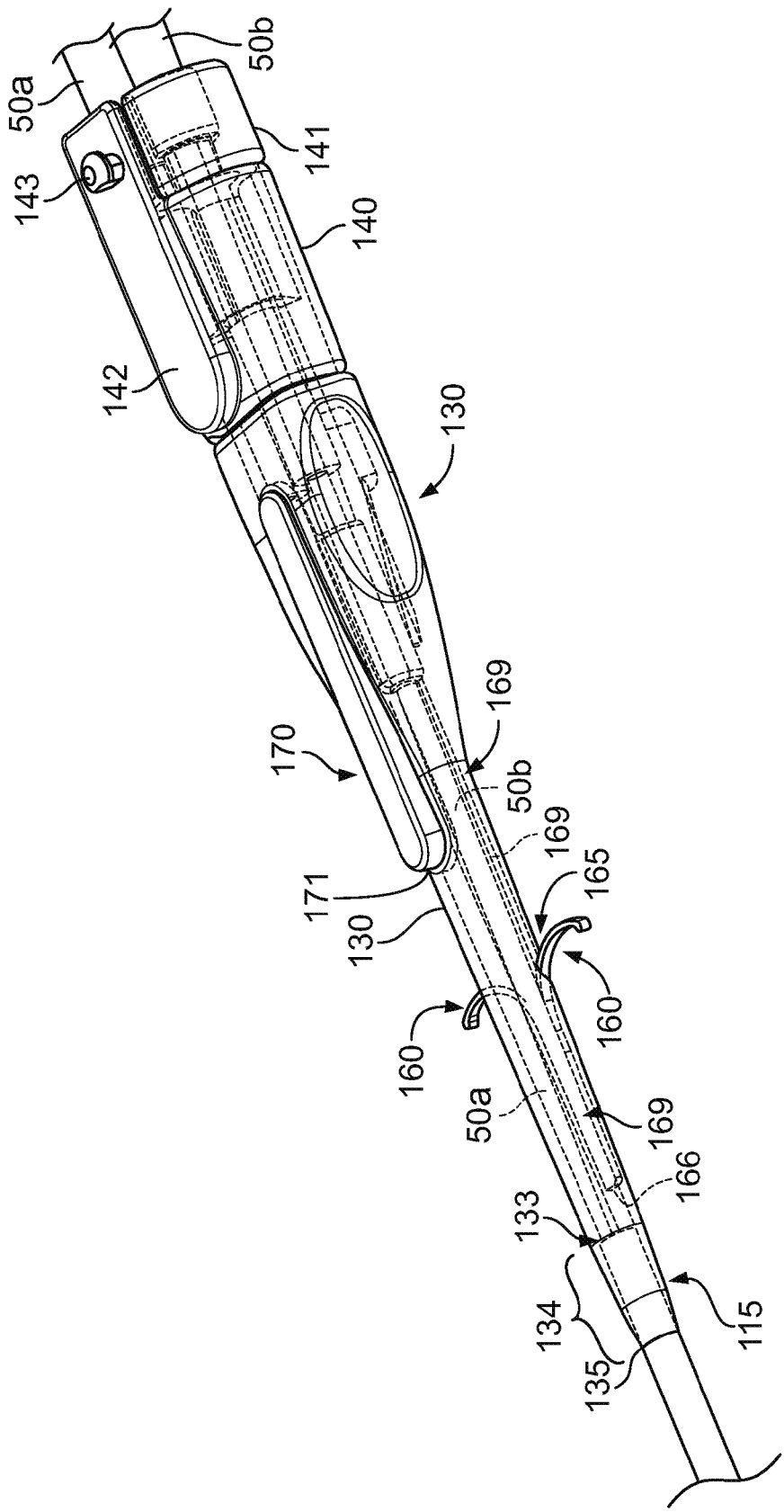
FIG. 7 is another perspective view of the medical anchor system of FIG. 1.

Referring to FIG. 7, as the actuator rod 164 slides forward inside of an actuator channel 169, the anchors 160 are retracted through the anchor deployment ports 165 and into the anchor device 100. In this embodiment, when an anchor tip portion 162 (FIG. 10) abuts a distal end 166 of the actuator channel 169, the anchors 160 become substantially encased within the anchor device 100. With the anchors 160 in the non-deployed configuration, the anchor device 100 may be withdrawn from the skin portion 20 by grasping a gripping portion 130 of the elongate body 110 and providing a withdrawing force. The likelihood of damaging the skin portion 20 can be reduced when the anchor device 100 is removed because the anchors 160 are arranged in the non-deployed configuration.

Referring now to FIGS. 7-10, the adjustment of the actuator 141 can cause one or more internal structures to move within the anchor device 100. For example, in this embodiment, the actuator 141 can be adjusted to cause the actuator rod 164 (FIG. 10) to move within the actuator channel 169. As shown in FIG. 7, the anchor device 100 can be arranged in the deployed and locked configuration so that the anchors 160 extend from an internal space within the elongate body 110 (as previously described in connection with FIG. 1). The elongate body 110 of the anchor device 100 can be made of a biocompatible material, such as PEEK (polyetheretherketone), polyethylene, polyimide, or the like. The elongate body 110 may include a tapered portion 134 along the distal tip portion 115 that facilitates insertion of the anchor device 100 through the skin penetration site 22. In this embodiment, the gripping portion 130 of the anchor device 100 includes a mesa 170 that forms an insertion stop, which may be used to inhibit insertion of the elongate body 110 into the skin portion 20 beyond a particular depth (so that the anchor ports 165 reside in the subcutaneous layer 24). In practice, as the elongate body 110 is advanced into the skin portion 20, a mesa wall 171 can abut a skin portion 20 surface when the elongate body 110 has been inserted substantially the appropriate distance to allow the anchors 160 to be deployed in the subcutaneous layer 24. In some embodiments, the mesa 170 can provide a surface onto which information about the medical device anchor system 10 can be indicated.

Figure 8B:
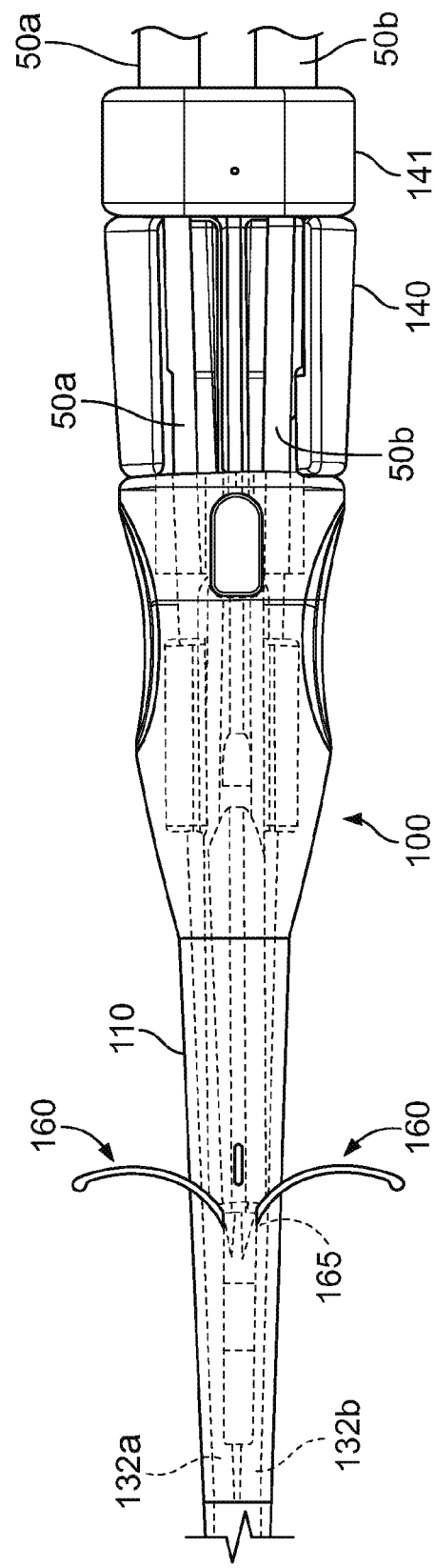
FIG. 8B is a bottom view of the medical anchor system of FIG. 1.
Figure 9:
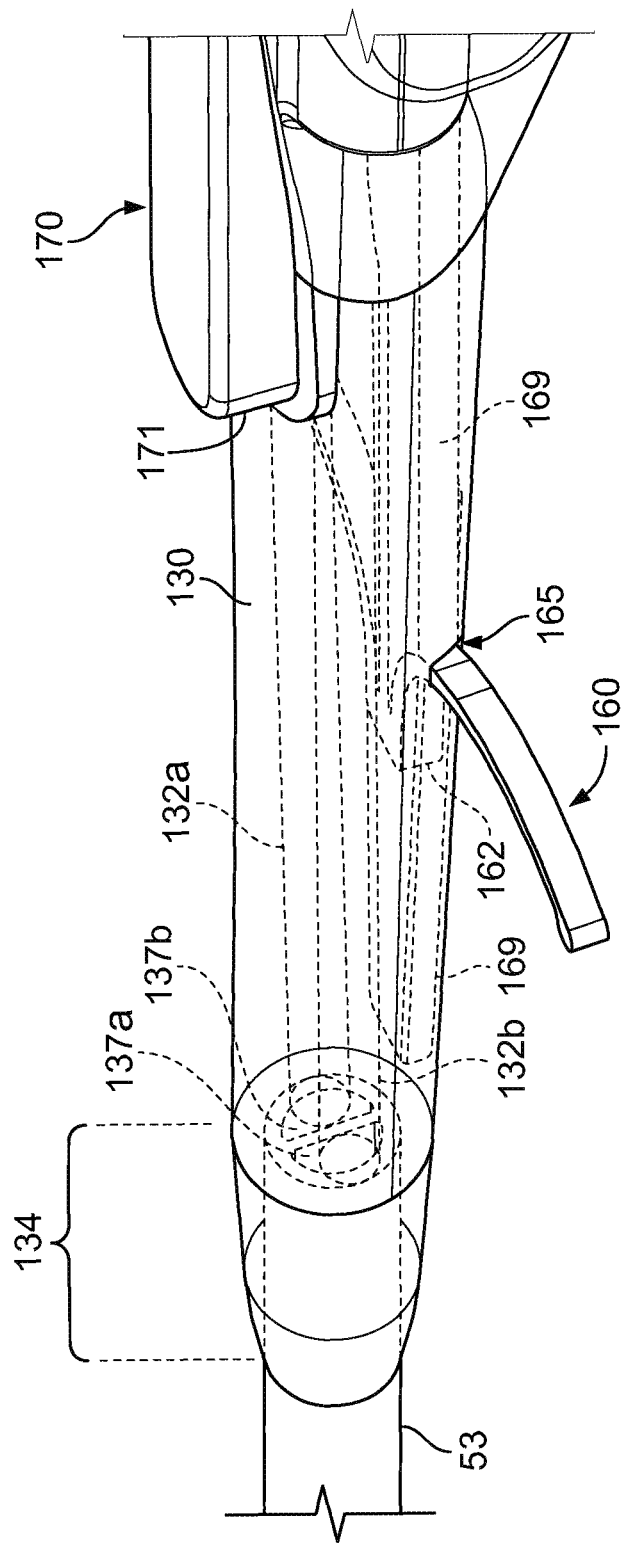
FIG. 9 is another perspective view of the medical anchor system of FIG. 1 showing selected internal structures of the system.

Referring now to FIGS. 8A, 8B, and 9, in some embodiments, the elongate body 110 can include one or more internal lumens 132a, 132b. The lumens 132a, 132b can be configured for fluid communication with catheter lines 50a, 50b or other medical instruments to allow transport of fluids from the catheter coupling members 51a, 51b to the distal catheter portion 53 (FIG. 1). In some implementations, internal lumens 132a, 132b are integral portions of catheter lines 50a, 50b that extend into the elongate body 110. In other implementations, the internal lumens 132a, 132b can be separate lumens, and a connection interface joins the internal lumens 132a, 132b with catheter lines 50a, 50b. In this embodiment, internal lumens 132a, 132b extend through the elongate body 110 and transition to a side-by-side position in the distal tip portion 115. After insertion of at least a portion of the elongate body 110 into the subcutaneous region 24 (FIG. 1), the internal lumens 132a, 132b can be used to introduce or sample fluids into or from a patient in cooperation with the distal catheter portion 53. In this embodiment, the distal catheter portion 53 includes two channels 137a, 137b (FIG. 9), each of which is coupled to a distal end of an internal lumen 132a, 132b respectively, thereby allowing fluid communication between the blood vessel 25 (FIG. 1), the distal catheter portion 53, the internal lumens 132a, 132b, and catheter lines 50a, 50b.

In some embodiments, the internal lumens 132a, 132b can have a diameter of about 3 French to about 30 French, and about 5 French to about 20 French, including particular ranges from about 3 French to about 7 French and about 12 French to about 17 French. In alternative embodiments of the anchor device 100, each internal lumen 132a, 132b can have a different shape or size. Furthermore, the multiple internal lumens 132a, 132b may be selectively sealable so that one internal lumen could be accessed while another is sealed. In some embodiments, this functionality can be achieved using the flow restriction devices 52a, 52b as described in relation to FIG. 1.

Referring to FIGS. 7-9, the anchor device 100 includes the actuator channel 169 and the ports 165 to facilitate the actuation of the anchors 160. The actuator channel 169 can be formed in the elongate body and is capable of receiving the actuator rod 164. The actuator channel 169 may be defined at least partially by one or more surfaces that can slidably engage the actuator rod 164 and anchors 160. Movement of the actuator rod 164 within the actuator channel 169 can urge the anchors 160 to extend from, or retract into, the anchor deployment ports 165. In this embodiment the actuator channel 169 may have a polygonal cross-sectional shape (e.g., quadrilateral or the like) that permits longitudinal movement of the actuator rod 164 while hindering possible rotational movement of the actuator rod 164 about its longitudinal axis.

The actuator channel 169 in this embodiment includes a distal portion near the distal tip portion 115 within the elongate body 110 that accepts a tip portion 162 of the actuator rod and at least a portion of the anchors 160 when the anchor device 100 is arranged in the non-deployed configuration. In this embodiment, when the tip portion 162 approaches the distal portion of the actuator channel 169, the anchors 160 approach the fully retracted (non-deployed) configuration and do not substantially extend from the anchor deployment ports 165. The actuator channel 169 and the internal lumens 132a, 132b may extend longitudinally along the elongate body 110 in a side-by-side configuration.

Referring now to FIG. 10, the actuator rod 164 may include an actuator shaft 164a that can be advanced and retracted within the actuator channel 169 in response to the movement of the actuator 141. In this embodiment, the anchors 160 are coupled to the actuator shaft 164a through a reduced portion 164b that is sized to fit adjacently between the anchors 160 in the distal portion of the actuator channel 169. Movement of the actuator 141 (and the corresponding translation of the actuator rod 164 within the actuator channel 169) causes the anchors 160 to shift between the non-deployed position (FIG. 2) and the deployed position (FIG. 3).

Referring back to FIGS. 7-9, in some cases, the actuator channel 169 may not fully extend through the elongate body 110 of the anchor device 100. For example, the actuator channel 169 may extend distally to a depth that extends to a terminal end (e.g., distal end 166) (FIG. 8A). In some embodiments, when the actuator 141 is shifted to the distal position (FIG. 2), the actuator rod 164 is caused to distally advance within the actuator channel 169 such that the tip portion 162 of the actuator rod 164 approaches the distal end 166 of the actuator channel 169, but may not abut the distal end 166. In this embodiment, the anchors 160 are coupled to the actuator rod 164 near the tip portion 162 so that the anchors 160 retract into the elongate body 110 as the anchor tip portion 162 of the actuator rod 164 approaches the distal end 166 of the actuator channel 169. In such circumstances, the anchors 160 may be flexed to a stressed condition while being retained within the actuator channel 169 or other internal space of the elongate body 110.

The actuator 141 can be adjusted to generate a longitudinal movement (e.g., longitudinal movement 190 (FIG. 3)), which is translated to the actuator rod 164 via a connector portion 167 (FIG. 10). In such circumstances, the actuator rod 164 may slide within the actuator channel 169 so that the tip portion 162 of the actuator rod 164 shifts away from the distal end 166 of the actuator channel 169. This motion of the actuator rod 164 causes the tips of the anchors 160 to pass through the anchor deployment ports 165 and to extend outwardly from the elongate body 110.

Referring again to FIG. 10, in some cases the actuator rod 164 can be coupled to the actuator 141 via a support shaft 197.

For example, the support shaft 197 can be coupled to actuator rod 164 using an overmolding process. In this embodiment, the actuator 141 provides support for a support shaft 197 as well as the swing arm 142 as described below. The actuator 141 in this embodiment includes catheter line supports 168a and 168b to support portions of the catheter lines 50a and 50b.

Accordingly, in this embodiment, the actuator rod 164 and the actuator 141 can be coupled so that the movement 135 of the actuator 141 results in a corresponding movement of the actuator rod 164. The connection can be configured to transmit longitudinal forces from the actuator 141 to the actuator rod 164, thereby directing the anchors 160 to extend from or retract into the elongate body 110 as previously described. The anchors 160 can be integrally formed with the actuator rod 164 (e.g., formed from a nitinol material or the like). It should be understood from the description herein that, in some embodiments, the anchors 160 can be joined with the actuator rod 164 at a location other than at the tip portion 162. For example, in other embodiments, the anchors 160 may be connected to the actuator rod 164 along a middle region of the actuator rod 164. Also, in alternative embodiments, the anchors 160 may be non-integral with the actuator rod 164. For example, the anchors 160 may be formed separately from the actuator rod 164 and then mounted to the actuator rod 164 using adhesives, welds, connectors, or the like.

Figure 12:
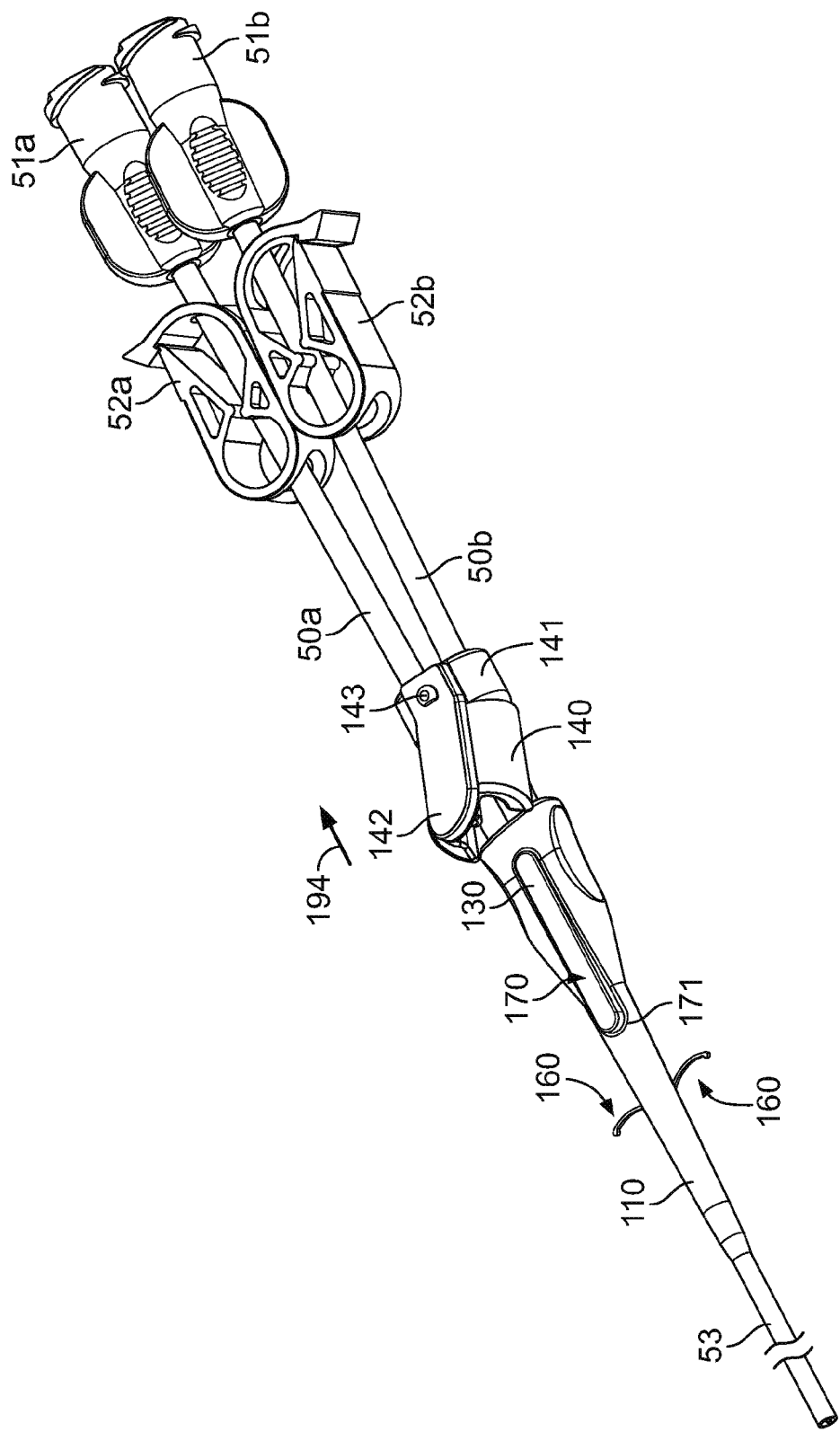
Figure 13:
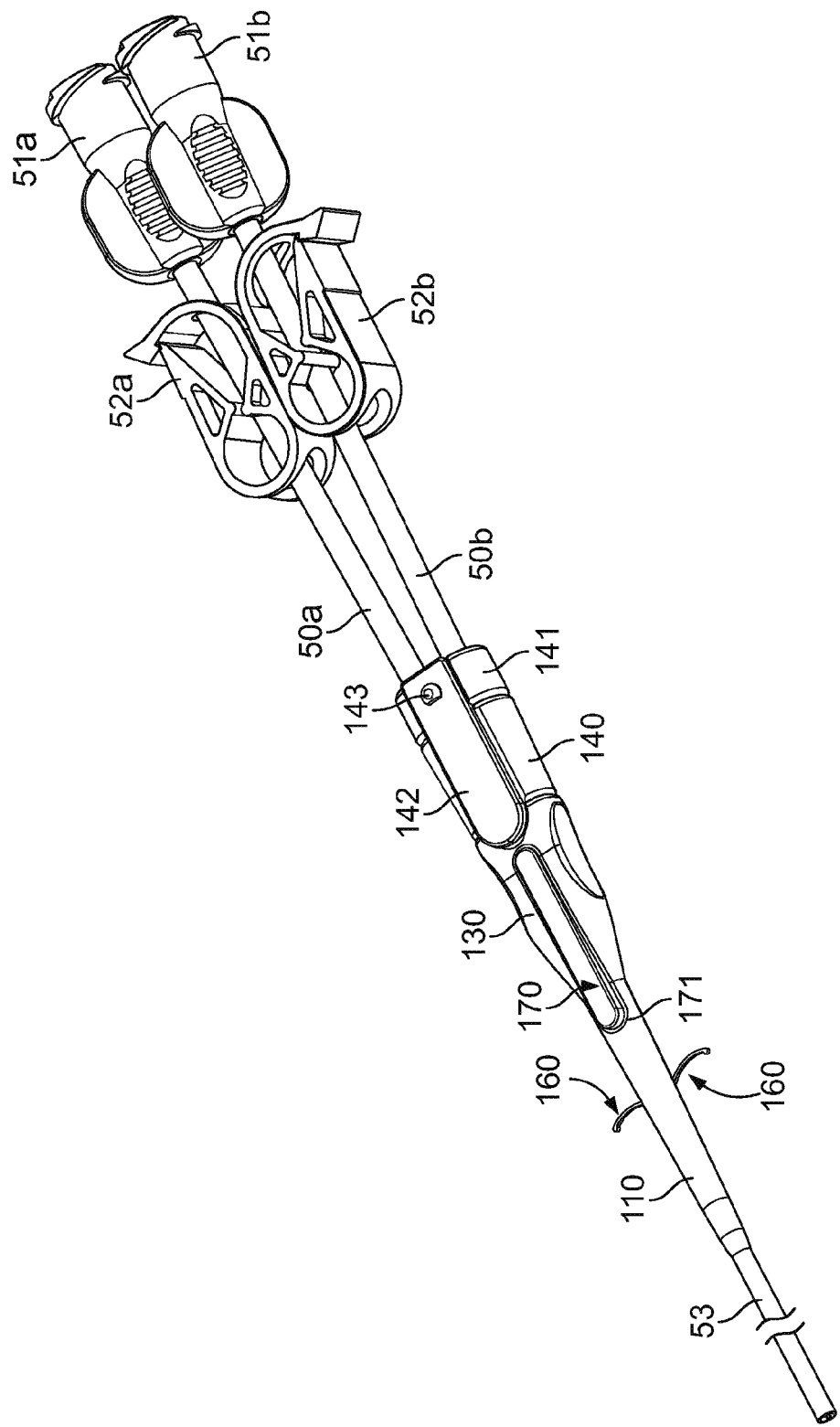

Referring now to FIGS. 11-13, in an alternative embodiment, the anchor device 100 can be adjusted from a non-deployed and non-locked configuration (FIG. 11) to a deployed and locked configuration (FIG. 13) without necessarily rotating the lock 140. In this embodiment, the actuator 141 slidably engages the catheter lines 50a, 50b and is coupled to the actuator rod 164 (FIG. 10), similar to previously-described embodiments. Deployable anchors 160 extend outwardly from the elongate body 110 when the actuator 141 is moved by linear translation 194 from a distal position (FIG. 11) to a proximal position (FIGS. 12 and 13). In this embodiment, when the actuator 141 is shifted from the distal position (FIG. 11) to the proximal position (FIG. 13), the anchors 160 deploy outwardly from ports 165. Similar to previously-described embodiments, the lock 140 provides a mechanism to prevent the actuator 141 from prematurely shifting from the proximal position to the distal position, which may then retract the anchors 160.

In this embodiment, the arm 142 is made from a resiliently flexible material that allows it to bend between a generally planar configuration (FIGS. 11 and 13) and a curved configuration (FIG. 12). When the actuator 141 is in the distal position (FIG. 11) the arm 142 becomes flexed such that the lock 140 correspondingly shifts to a position adjacent to an outer surface of the elongate body 110. When the actuator 141 is shifted to the proximal position (FIG. 13) the lock 140 can correspondingly shift to a proximal position that allows the lock 140 to engage with the catheter lines 50a, 50b as previously described and shown in FIG. 13. As such, the lock 140 can fit snugly between the actuator 140 and the elongate body 110 to retain the actuator 141 in the active position. When the actuator 141 is shifted to the proximal position (FIG. 13), the anchors 160 are deployed as previously described. In this embodiment, the arm 142 may not necessarily rotate about a pivot pin, and instead may be fastened to the actuator 141 to allow it to be shifted between a generally planar and a curved or non-planar configuration. In some cases, the arm 142 can be riveted in place to reduce the likelihood inadvertent rotation.

Accordingly, the user can readily deploy the anchors 160 into the subcutaneous layer 24 of the skin portion 20 by adjusting the actuator 141 and snapping the lock 140 into position. For example, a physician may advance the anchor device 100 into the skin portion 20 and deliver the distal catheter portion 53 in a targeted blood vessel 25. Then the physician can, for example, grasp the gripping portion 130 of the elongate body 110 while sliding the actuator 141 from the distal (FIG. 11) to the proximal (FIG. 13) position, thereby deploying the anchors 160 into the subcutaneous layer 24. The physician may contemporaneously exert a pressing force on the arm 142 (and the lock 140) so as to snap the lock 140 down upon the catheter lines 50a, 50b to reduce the likelihood of prematurely moving the actuator 141 and retracting the anchors 160.

Figure 14:
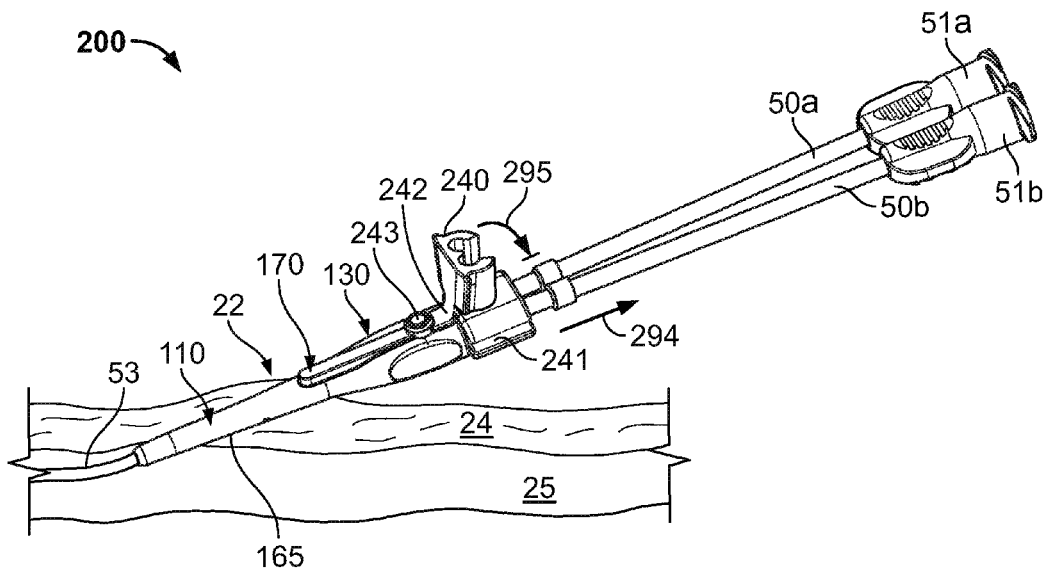
FIGS. 14-15 are perspective views of a medical anchor system having a subcutaneous anchor mechanism, in accordance with alternative embodiments.
Figure 15:
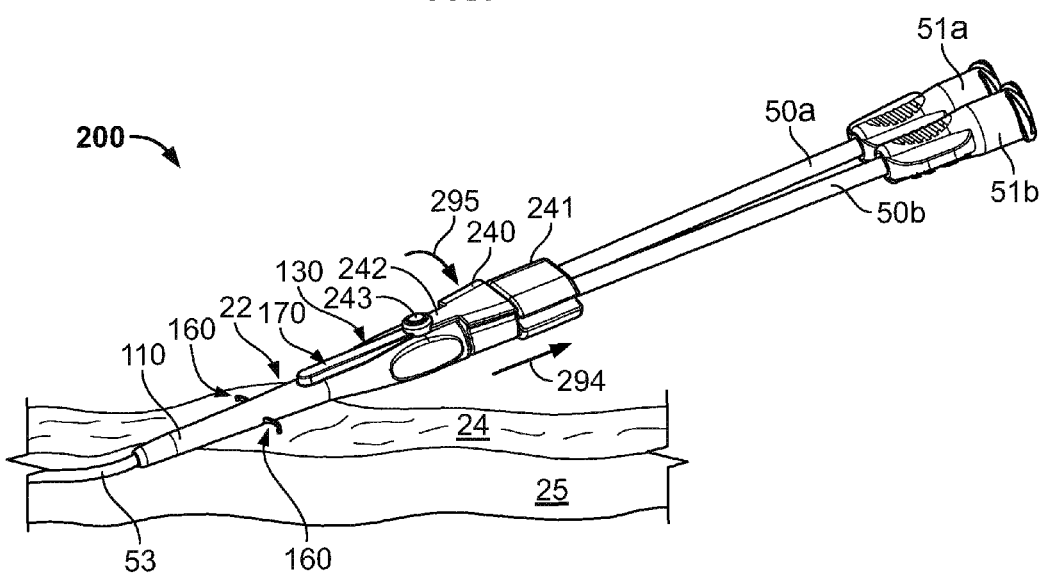

Referring now to FIGS. 14-15, some alternative embodiments of an anchor device 200 can include a lock 240 that is movably attached to a catheter hub body (e.g., the elongate body 110 in the depicted embodiment). As such, the lock 240 can be readily adjusted relative to the actuator 241 so as to retain the actuator 241 in a deployed and locked configuration (FIG. 15). For example, the user may grasp the actuator 241 with his or her fingers to pull in a longitudinal path 294 while readily pushing the lock 240 with his or her thumb in a downward motion 295. Accordingly, the lock 240 can be arranged between the catheter hub body (e.g., elongate body 110 in this embodiment) and the actuator 241 when the flexible anchors 160 are deployed in the subcutaneous layer 24. In such circumstances, the lock 240 can reduce the likelihood of the actuator 241 prematurely shifting from the proximal position to the distal position to thereby inadvertently retract the anchors 160.

Similar to previously described embodiments, the anchor device 200 may include a number of catheter lines 50a, 50b that extend from catheter coupling members 51a, 51b toward the elongate body 110. The elongate body 110 can provide fluid communication between the catheter lines 50a, 50b and the distal catheter portion 53 that is delivered into a targeted body vessel 25. Also similar to previously described embodiments, the actuator 241 of the anchor device 200 can be coupled to the actuator rod 164 (FIG. 10) so as to deploy anchors 160 in the subcutaneous layer 24 when the elongate body 110 is passed into the skin penetration point 22. As previously described, the anchors 160 extend outwardly from the elongate body 110 when deployed from the ports 165 into the subcutaneous layer 24.

Still referring to FIGS. 14-15, the anchor device 200 can be adjusted from the deployed and non-locked configuration (FIG. 14) to a deployed and locked configuration (FIG. 15). In some embodiments, the lock 240 can provide a mechanical bracing force between the actuator 241 and a proximal surface of the elongate body 110 to thereby retain the actuator 241 in the active or deployed position (FIG. 15) throughout the medical procedure. In this embodiment, lock 240 is coupled to an arm 242 that is attached to the elongate body 110 at a connection point 243. The arm 242 can comprise a resiliently flexible material that allows it to bend to and from a generally planar configuration (FIG. 14). For example, the lock 240 and the swing arm 242 can be integrally molded from a flexible polymer material. The lock 240 may include curved portions that substantially mate with an outer circumference of catheter lines 50a-b, thus reducing the likelihood of the lock 240 rotationally shifting from the locked position without user intervention. When the actuator 241 is in the distal position (FIG. 14), the arm 242 can be flexed or otherwise manipulated such that the lock 240 correspondingly shifts to a position adjacent to an outer surface of the actuator 241. When the actuator 241 is shifted to the proximal position (FIG. 15), the lock 240 can correspondingly shift to an intermediate position between the elongate body 110 and the actuator 241. As such, the lock 240 can fit snugly between the actuator 241 and the elongate body 110 to retain the actuator 241 in the active position, which causes the anchors 160 to remain deployed as previously described. The arm 243 may pivot relative to the elongate body 110 about the connection point 243. Alternatively, the arm 242 may instead be fixed to the elongate body so that it can flexibly adjust between a generally planar and a non-planar configuration.

The anchor device 200 can be adjusted from the non-deployed and non-locked configuration (FIG. 14) to a deployed and locked configuration (FIG. 15) by first disengaging the lock 140 from catheter lines 50a, 50b while the lock 140 is in the proximal position. This may be accomplished, for example, by moving the actuator 241 in a longitudinal path 294 away from the elongate body 110 so that the anchors 160 are deployed into the subcutaneous layer 24. When the actuator 241 is moved in the longitudinal path 294 away from the elongate body, a gap is created therebetween. As such, the lock 240 can be pressed in a downward path 295 (or a pivoting path) into the space between the actuator 241 and the elongate body 110 so as to fit snugly between the elongate body 110 and the actuator 241. As such, the lock 240 retains the actuator 241 in a substantially stationary position relative to the elongate body 110, thereby maintaining the deployed position of the anchors 160. This configuration can reduce the likelihood of the actuator 241 prematurely shifting to a distal position (and premature withdrawal of the anchors 160).

In this embodiment, when the anchor device 200 is in a deployed and locked configuration (FIG. 15), various fluid delivery and sampling systems can be coupled with the anchor device 200. For example, blood may be drawn from the catheter lines 50a, 50b; likewise, medications can be introduced into a patient's blood vessel 25 via the one or more catheter lines 50a, 50b and the distal catheter portion 53. The anchor device 200 may remain attached to the patient for an extended period of days, weeks, or months.

To remove the anchor device 200 from the skin, the process described for inserting the anchor device 200 (refer to FIGS. 14-15) can generally be reversed. For example, in this embodiment, to remove the anchor device 200 from the skin, the lock 240 can be lifted so as to disengage the actuator 241. With the lock 140 in a disengaged position, the actuator 241 is free to shift from the proximal position to the distal position (FIG. 14), which has the effect of applying a translational force to the internal actuator rod 164 (FIG. 10) and retracting the anchors 160 into the ports 165. thereafter, the anchor device 200 can be safely withdrawn from the skin in a manner that reduces the likelihood of trauma to the surrounding tissue.

A number of embodiments have been described. Nevertheless, it will be understood that various modifications may be made without departing from the spirit and scope of the disclosed embodiments. Accordingly, other embodiments are within the scope of the following claims.

What is claimed is:

1. A method for subcutaneously anchoring a catheter instrument, comprising:
    inserting a distal catheter line of a catheter hub body through a skin penetration point, wherein the catheter hub body provides fluid communication between a first proximal external line connected to the catheter hub body and a first lumen of the distal catheter line and provides fluid communication between the second proximal external line connected to the catheter hub body and a second lumen of the distal catheter line;
    adjusting a pair of subcutaneous anchor elements from a non-deployed orientation in which the subcutaneous anchor elements are housed inside the catheter hub body to a deployed orientation in which free ends of the subcutaneous anchor elements extend outwardly away from the catheter hub body in a subcutaneous layer proximate to the skin penetration point, wherein the pair of subcutaneous anchor elements are adjusted to the deployed orientation by moving an actuator relative to the catheter hub body; and
    moving a locking device to a locked position to releasably maintain the pair of subcutaneous anchor elements in the deployed orientation,
    wherein the first and second proximal external lines, at least a portion of the actuator, and the locking device remain external to the skin penetration point after the distal catheter line and the pair of subcutaneous anchor elements are inserted through the skin penetration point.

2. The method of claim 1, further comprising releasably connecting a first fluid cannula with a first catheter coupling member at a proximal end of the first proximal external line, and releasably connecting a second fluid cannula with a second catheter coupling member at a proximal end of the second proximal external line.

3. The method of claim 1, wherein the catheter hub body has a greater lateral width at a proximal end than at a distal end, wherein the first and second proximal external lines are connected to the proximal end of the catheter hub body in a generally side-by-side position, wherein the distal catheter line is connected to the distal end of the catheter hub body, and wherein the pair of subcutaneous anchor elements are positioned between the proximal end and the distal end of the catheter hub body.

4. The method of claim 1, wherein the actuator comprises a slider instrument, the method further comprising sliding the actuator along a portion of the first and second proximal external lines at a location proximal of a proximal end of the catheter hub body.

5. The method of claim 4, wherein the locking device is movably connected to the slider instrument of the actuator.

6. The method of claim 1, wherein the actuator includes an actuator rod that extends through an actuator channel defined inside the catheter hub body and that is coupled with the anchor elements.

7. The method of claim 1, wherein the anchor elements are adjusted to the deployed orientation, each of the anchor elements extends outwardly to a rounded tip.

8. The method of claim 1, wherein at least a portion of each anchor element exhibits superelasticity when shifted from the non-deployed orientation to the deployed orientation.

9. The method of claim 1, wherein moving the locking device to the locked position causes the locking device to limit movement of the actuator relative to the catheter hub body and hinders migration the flexible anchors from the deployed position toward the non-deployed position.

10. The method of claim 9, wherein moving the locking device to the locked position causes the locking device to be friction fit between a proximal end of the catheter hub body and a distal facing surface of the actuator.

11. The method of claim 1, wherein a first flow restriction device is coupled to the first proximal external line at a position proximal to the catheter hub body, and a second flow restriction device is coupled to the second proximal external line at a position proximal to the catheter hub body.

12. The method of claim 1, further comprising releasably connecting a first catheter coupling member at a proximal end of the first proximal external line with a first fluid cannula, and releasably connecting a second catheter coupling member at a proximal end of the second proximal external line with a second fluid cannula.

13. The method of claim 1, wherein the catheter hub body has a greater lateral width at the proximal end than at the distal end.

14. The method of claim 13, wherein the flexible anchors are positioned between the proximal end and the distal end of the catheter hub body.

15. The method of claim 1, wherein the flexible anchors each have a curved shape when adjusted to the deployed orientation, the curved shape including a convexly curved portion facing toward the proximal end of the catheter hub body.

16. The method of claim 1, wherein the actuator includes an actuator rod that extends through an actuator channel defined inside the catheter hub body and that is coupled with the flexible anchors.

17. The method of claim 1, wherein when the flexible anchors are adjusted to the deployed orientation, each of the flexible anchors extends outwardly to a rounded tip.

18. The method of claim 1, wherein the catheter hub body comprises a tapered portion along the distal end.

19. The method of claim 1, wherein the catheter hub body defines side-by-side internal lumens that extending longitudinally from the proximal end of the catheter hub body toward the distal end of the catheter hub body.

20. The method of claim 19, wherein the internal lumens have a lumen diameter of 5 French to about 20 French.

* * * * *